US008771175B2

(12) United States Patent
Schostek et al.

(10) Patent No.: US 8,771,175 B2
(45) Date of Patent: Jul. 8, 2014

(54) CAPSULE TYPE ENDOSCOPE INCLUDING MAGNETIC DRIVE

(75) Inventors: Sebastian Schostek, Tuebingen (DE); Fabian Rieber, Stuttgart (DE); Philipp Troebner, Tuebingen (DE); Marc Oliver Schurr, Tuebingen (DE)

(73) Assignee: Novineon Healthcare Technology Partners GmbH, Tuebingen (DE)

( * ) Notice: Subject to any disclaimer, the term of this patent is extended or adjusted under 35 U.S.C. 154(b) by 245 days.

(21) Appl. No.: 13/011,795

(22) Filed: Jan. 21, 2011

(65) Prior Publication Data

US 2011/0184235 A1 Jul. 28, 2011

(30) Foreign Application Priority Data

Jan. 22, 2010 (EP) .................................... 10000644

(51) Int. Cl.
*A61B 1/04* (2006.01)
(52) U.S. Cl.
USPC .............................. 600/117; 600/118; 600/130
(58) Field of Classification Search
None
See application file for complete search history.

(56) References Cited

U.S. PATENT DOCUMENTS

| 6,939,290 | B2* | 9/2005 | Iddan .......................... 600/109 |
| 7,727,269 | B2* | 6/2010 | Abraham-Fuchs et al. . 623/1.11 |
| 2005/0038370 | A1* | 2/2005 | Kuth et al. ....................... 602/78 |
| 2005/0062562 | A1* | 3/2005 | Ries ................................. 335/1 |
| 2007/0161862 | A1* | 7/2007 | Yokoi et al. ..................... 600/175 |
| 2007/0191671 | A1* | 8/2007 | Kawano et al. .................. 600/12 |
| 2007/0221233 | A1* | 9/2007 | Kawano et al. ................ 128/899 |
| 2007/0244388 | A1* | 10/2007 | Sato et al. ....................... 600/424 |
| 2007/0270628 | A1* | 11/2007 | Kawano et al. .................. 600/12 |
| 2008/0183041 | A1* | 7/2008 | Fujimori et al. ................ 600/118 |
| 2008/0294006 | A1* | 11/2008 | Uchiyama et al. .............. 600/118 |
| 2008/0300458 | A1* | 12/2008 | Kim et al. ....................... 600/118 |
| 2009/0012363 | A1* | 1/2009 | Liu et al. ......................... 600/127 |
| 2009/0048484 | A1* | 2/2009 | Swain et al. .................... 600/118 |
| 2009/0171146 | A1* | 7/2009 | Fujita ............................. 600/102 |
| 2009/0281387 | A1* | 11/2009 | Takizawa et al. .............. 600/117 |
| 2010/0056866 | A1* | 3/2010 | Uchiyama et al. .............. 600/118 |
| 2011/0184235 | A1* | 7/2011 | Schostek et al. ............... 600/109 |

OTHER PUBLICATIONS

Communication pursuant to Article 94(3) EPC in European Patent Application No. 10 000 644.4, dated Jul. 16, 2012.

* cited by examiner

*Primary Examiner* — Anhtuan T Nguyen
*Assistant Examiner* — Jae Woo
(74) *Attorney, Agent, or Firm* — AlbertDhand LLP

(57) ABSTRACT

The present invention discloses a magnet driven capsule type endoscope comprising an image recording unit as well as an image data processing unit, a position sensor for providing data about the position of the capsule type endoscope with respect to the direction of gravitation, a data transmitting unit, an energy source for supplying the units and the sensor with energy and a permanent magnet. In accordance with the invention, the permanent magnet is arranged offset with respect to the center of gravity and to the geometrical center of the capsule type endoscope.

3 Claims, 9 Drawing Sheets

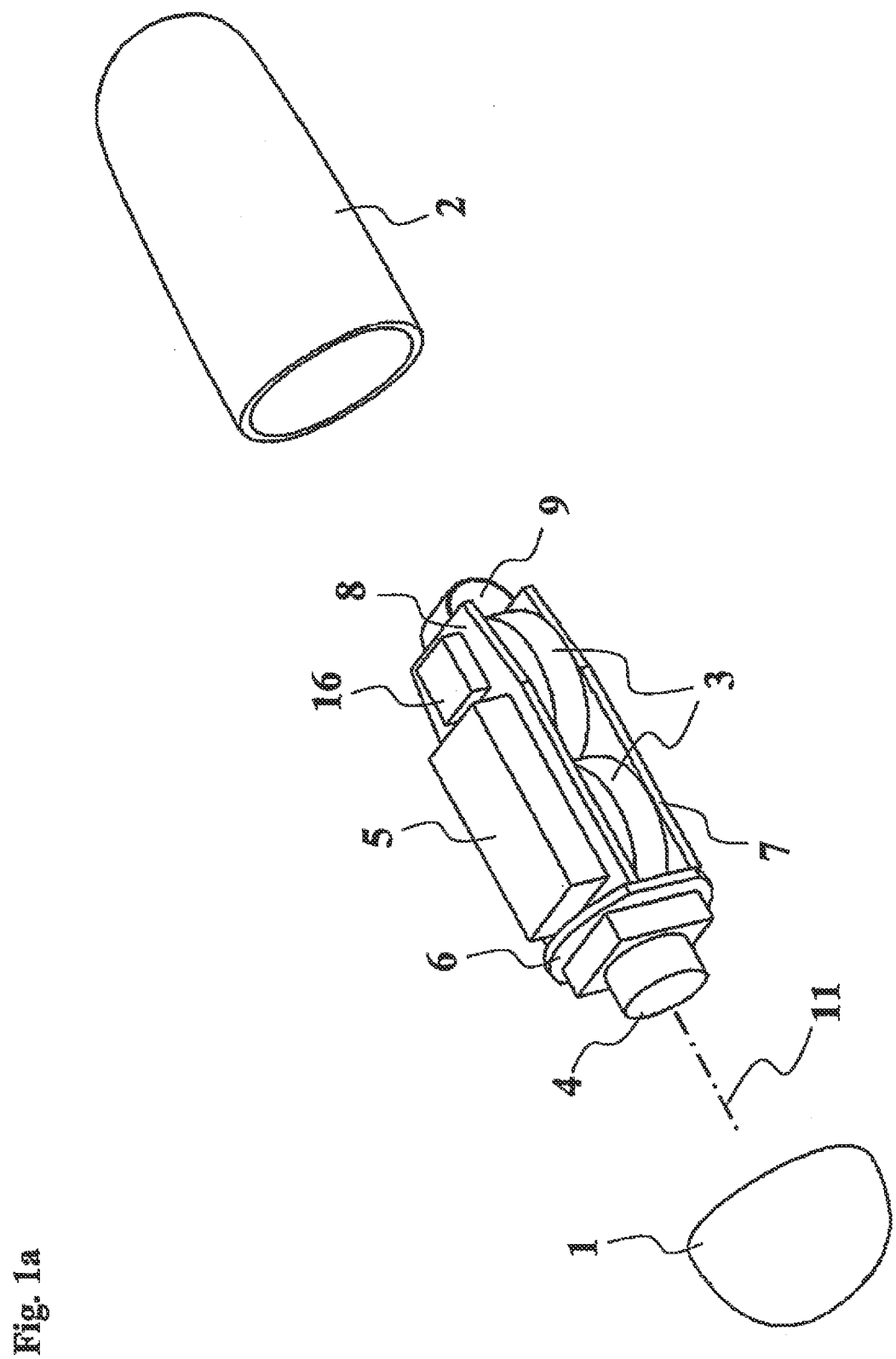

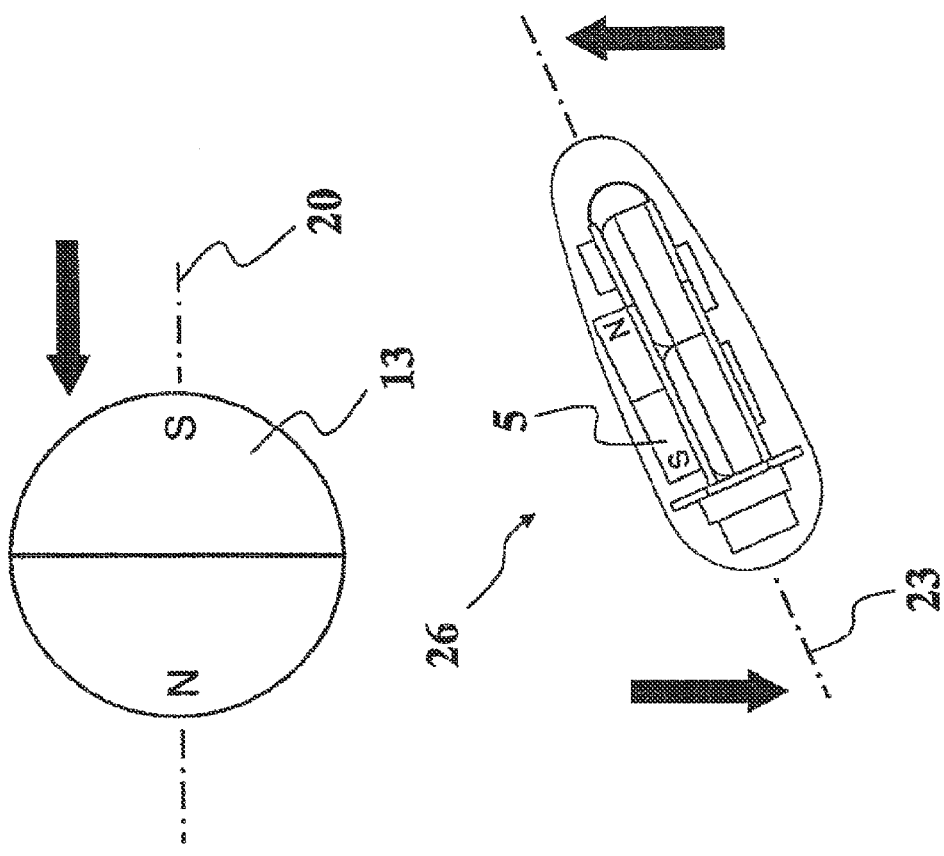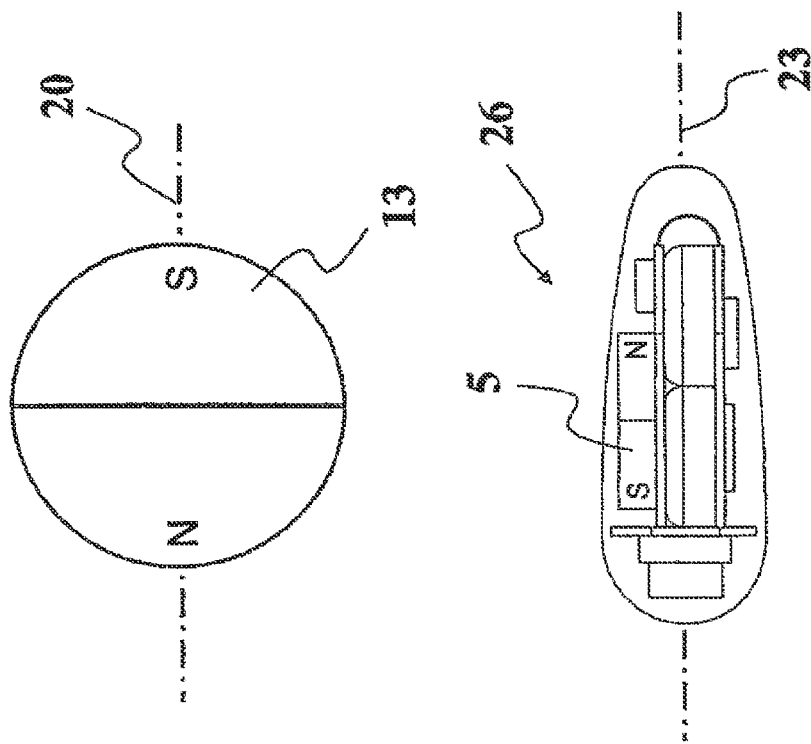

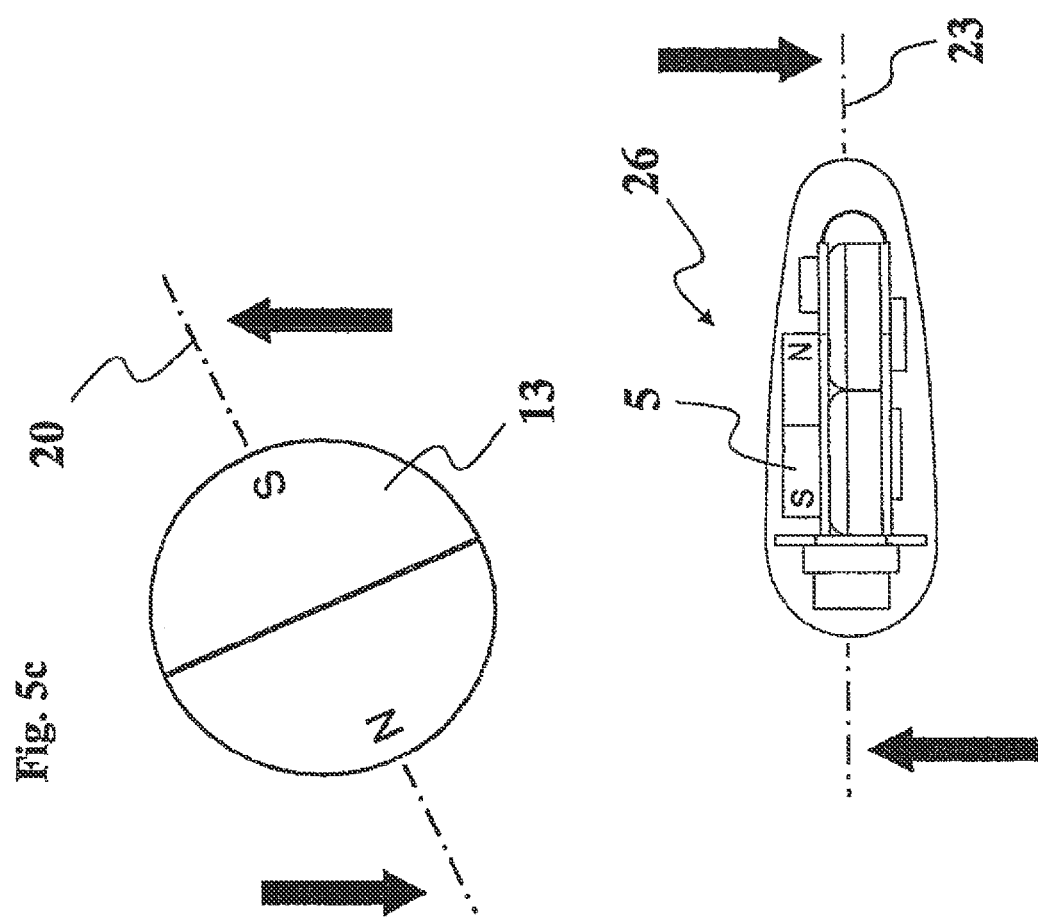

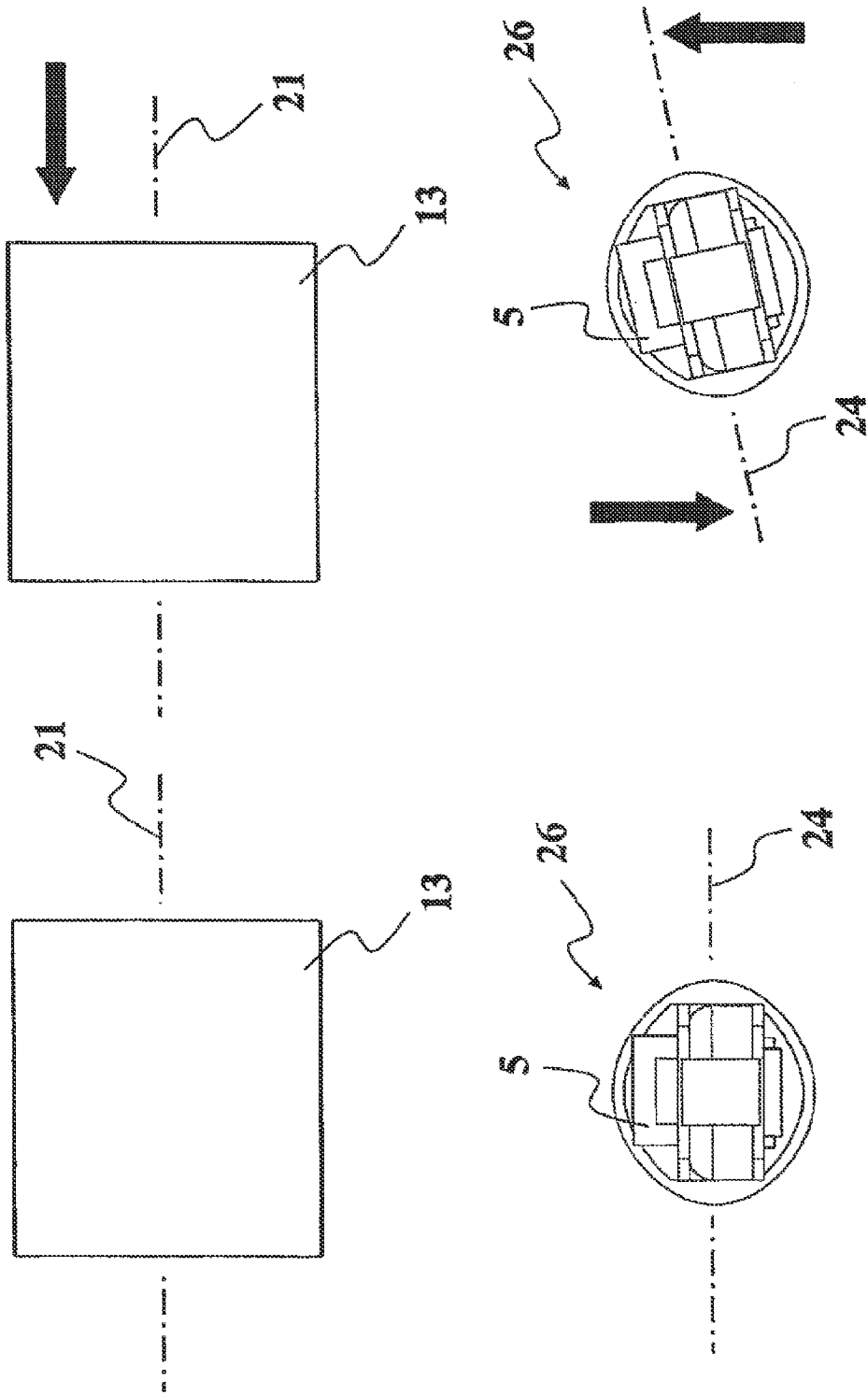

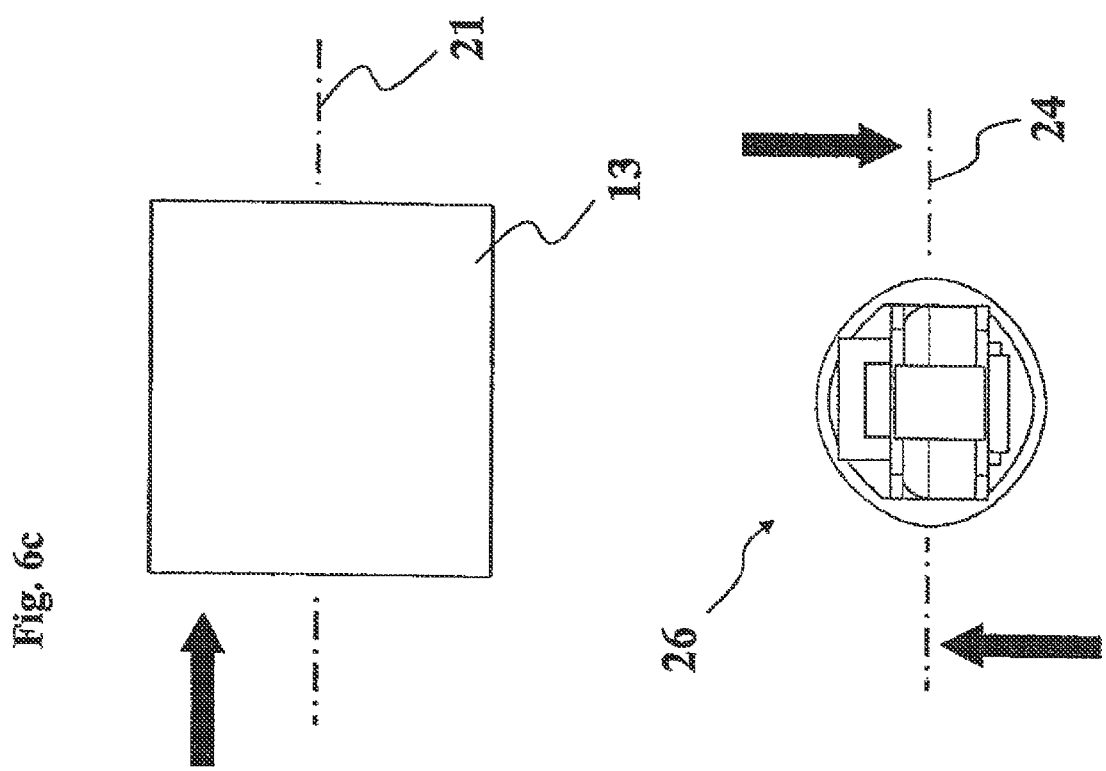

CAPSULE TYPE ENDOSCOPE INCLUDING MAGNETIC DRIVE

The present invention relates to a capsule type endoscope including a magnetic drive.

Magnetically driven capsule type endoscopes are endoscopes that are swallowed by a patient like a pill or a capsule and are then advanced in the intestinal tract substantially by the natural peristaltic motion. In addition, a magnetic drive comprising a capsular magnet and an extracorporeal magnet is provided so that the movement and the orientation of the capsule can be influenced.

Hereinafter as capsular magnet a device integrated in the capsule which is adapted to generate a magnetic field of known polarization is perceived also concerning the invention. For this purpose both a solenoid and a permanent magnet as well as a combination of single or plural one of the said two possibilities are suited. This device may also consist of plural permanent magnets or plural solenoids whose magnetic fields superpose to form a resulting magnetic field.

Hereinafter also concerning the invention as an extracorporeal magnet a device provided outside the examination space subject to inspection by the capsule type endoscope is perceived which is adapted to generate a magnetic field of known polarization. For this purpose both a solenoid and a permanent magnet as well as a combination of single or plural ones of the said afore-mentioned possibilities are suited. This device may also consist of plural permanent magnets or plural solenoids whose magnetic fields superpose to form a resulting magnetic field.

Hereinafter also concerning the invention spaces which are inspected by a capsule type endoscope are perceived as examination space. In the case of medical applications these are understood to be hollow organs or hollow spaces in the human or animal body into which a capsule type endoscope can be introduced. In the case of technical applications these are understood to be hollow spaces in technical systems into which a capsule type endoscope can be introduced.

The terms of endoscopic capsule and capsule type endoscope are equivalent.

Capsule type endoscopes for inspection of the intestinal tract at present available on the market are advanced exclusively passively inside the body by the peristaltic motion and the body motion. The camera integrated in the capsule therefore takes random pictures of the organ wall. By reason of the missing active control of such a capsule type endoscope, passive capsule type endoscopes have stood the clinical test merely for the inspection of the esophagus and the small intestine, because the capsule body is adapted to completely open the lumen of these organs so that the organ wall can be detected substantially completely by the integrated camera during the passive passage. By the way, today cameras for endoscopes are equipped with a so-called "fish-eye" technology permitting a panorama view of up to 180°.

However, the inspection of the stomach and the large intestine is clinically by far more significant than the inspection of the esophagus and the small intestine. In the stomach and the colon the endoscopic check-up plays an important role especially for the early detection of cancer. Today this check-up is substantially carried out by flexible endoscopy with an endoscope shaft being inserted from the anus into the intestines or through the mouth into the stomach of a patient.

An actively controllable endoscopic capsule could facilitate an endoscopic check-up of the stomach and the colon with definitely improved convenience for the patient.

The active control in accordance with a check of motion and orientation through external magnetic fields was described already in DE 3 440 177. In this case a permanent magnet integrated in the endoscopic capsule permits a motion and orientation control of the capsule by externally generated magnetic fields. These fields can be generated by coils or by a second extracorporeal permanent magnet.

Using a permanent magnet as an extracorporeal magnet entails the advantage of a simple extracorporeal structure for the capsule control. By making use of rare-earth magnets magnetic fields of appropriate force can be generated. In contrast to a coil system preferably comprising an assembly of air-core coils adapted to generate a homogenous magnetic field over a larger volume, when using a permanent magnet or a comparatively compact solenoid as extracorporeal magnet the position and orientation of the extracorporeal magnet relative to the intracorporeal magnet is very important. The reason for this is that when using air-core coils of appropriate size the volume inside the coils can be utilized to actuate the capsule type endoscope. In contrast to that, when making use of a permanent magnet or a comparatively compact solenoid the volume outside the magnet is available for actuating the capsule type endoscope. Such extracorporeal magnet therefore can be described as a point-shaped magnetic field source compared to a coil system. Therefore, when using a permanent magnet or a comparatively compact solenoid as extracorporeal magnet, the orientation of the extracorporeal magnet relative to the magnet inside the capsule type endoscope plays a crucial role.

The use of a permanent magnet as magnet inside the capsule has the advantage of a simple capsule structure. In contrast to a solenoid, a permanent magnet requires no energy supply to maintain the magnetic field.

Although the capsule supplies endoscopic images, there is no clue given as to its position and orientation in the spatial reference system of the extracorporeal magnet. For a control of an endoscopic capsule including an integrated capsular magnet by an extracorporeal magnet, however, knowledge about the relative position between the endoscopic capsule and the extracorporeal magnet are indispensable in order to be able to move the extracorporeal magnet into the correct direction and in the correct way.

From prior art therefore further capsule type endoscopes of this species dealing with these problems are known.

For instance, US 2008/0300458 discloses a capsule type endoscope comprising an integral permanent magnet and an extracorporeal permanent magnet. The capsular magnet is aligned coaxially with respect to the central axis of the cylindrical capsule concerning its north-south axis, wherein the extracorporeal magnet is arranged likewise coaxially with respect to the capsular magnet (though in reverse orientation) concerning its north-south axis. When the extracorporeal magnet is moved in the longitudinal direction of the capsule, the capsule is entrained and hereby simultaneously a (coupled) tilting motion is imparted about (not around) its longitudinal axis. This tilting motion can be basically compensated by a counter-rotation of the extracorporeal magnet. When, moreover, the extra-corporeal magnet is moved sideways, the capsule likewise follows this movement. An occurring (coupled) roving motion of the capsule around (not about) the longitudinal axis thereof cannot be compensated by this system, however.

An embodiment alternative hereto shown in US 2008/0300458 provides to dispose the capsule type magnet in the capsule such that the north-south axis thereof is oriented normal to the longitudinal axis of the capsule. In this case, a rolling motion of the capsule in the event of a sideward movement of the extracorporeal magnet can be basically compensated by tilting the same about (not around) its north-south axis. It is no longer possible, though, to compensate a (coupled) tilting motion of the capsule when moving the extracorporeal magnet in the longitudinal direction of the capsule. For the rest, in US 2008/0300458 the problem of providing information about the relative position between extracorporeal and intracorporeal permanent magnets is not dealt with.

Moreover, from DE 10 2007 030 747 A1 a magnetically driven capsule type endoscope is known comprising a cylindrical capsule in which an image-recording as well as image data processing unit, a data transmitting unit, an energy source and a permanent magnet are accommodated. In accordance with a schematic diagram contained in DE 10 2007 030 747 A1, the north-south axis of the permanent magnet is oriented in the longitudinal direction of the capsule.

Finally US 2004/0050395 A1 discloses a magnetically guided capsule type endoscope comprising a cylindrical capsule in which at least one permanent magnet is arranged so that the north-south axis thereof is oriented coaxially with respect to the central axis of the capsule. Furthermore, a detector is arranged to detect the position and orientation of the capsule in the hollow space of a patient.

Although accordingly a plurality of capsule type endoscopes having a magnetic drive are known from prior art which are adapted to three-dimensionally control the movement of the capsule also using positional sensors, all capsule solutions constitute a compromise of the controllability between the tilting motion and the rolling motion. In other words, a plurality of capsule type endoscopes provides a control of the tilting motion about (not around) the longitudinal axis of the capsule which is triggered upon a magnetically guided longitudinal movement of the capsule. Other endoscopes have a rolling motion control to influence a rolling motion of the capsule around (not about) the longitudinal axis thereof induced upon a magnetically guided sideways movement of the capsule. A complete movement control is not possible, however, in the capsule type endoscopes according to prior art. Furthermore, the prior art reveals no satisfactory solution to determine the exact position of the capsule type endoscope relative to the extracorporeal magnet, which is required for an exact compensation of motion, however.

The orientation of an endoscopic capsule including an integrated magnet having a fixed direction of polarization by the movement of an extracorporeal magnet has basic restrictions, because merely two degrees of freedom can be actuated to orient the capsule type endoscope. Assuming that a capsule type endoscope includes an integrated magnet (in accordance with the afore-mentioned prior art) whose polarization is oriented in parallel to the X-axis of the Cartesian coordinate system of the endoscopic capsule, the orientation of the endoscopic capsule can be controlled exclusively around the Y-axis and the Z-axis. In this case, a rotation of the capsule around the X-axis does not entail a change of orientation of the polarization of the magnet inside the capsule relative to the polarization of a magnetic field generated extracorporeal. The orientation of the capsule type endoscope around its X-axis therefore cannot be controlled by actuating the magnetic field generated extracorporeally. From prior art no technical solution is known which permits a control of the orientation of an endoscopic capsule having an integrated magnet of a fixed direction of polarization around all three axes of the Cartesian coordinate system of the endoscopic capsule by the movement of an extracorporeal magnet.

In view of this prior art, it is the object of the invention to provide a capsule type endoscope driven by a magnet and an endoscopic device exhibiting higher functionality. It is a particular object of the invention to improve the positioning capability of the capsule type endoscope, especially by permitting the controllability of the orientation of an endoscopic capsule including an integrated magnet around all three axes of the Cartesian coordinate system of the endoscopic capsule, and to increase the examination accuracy in this way.

This object is achieved by a capsule type endoscope comprising the features of claim 1 and an endoscopic device comprising the features of claim 9. Advantageous further developments of the invention are the subject matter of the subclaims.

Accordingly, it is the core of the invention to equip the capsule type endoscope with an image recording unit and an image data processing unit, a position sensor to provide data about the position of the capsule type endoscope with respect to the direction of gravitation, a data transmitting unit, an energy source for the energy supply of the units and the sensor and a capsular magnet, preferably a permanent magnet. In accordance with the invention, the capsular magnet is arranged at least peripherally with respect to a central axis of the capsule type endoscope. In accordance with the invention, the polarization (north-south direction) of the capsular magnet is oriented preferably in the direction of the image recording unit. In particular, by virtue of its peripheral location the capsular magnet is arranged offset with respect to both the center of gravity and the geometrical center of the capsule type endoscope.

As geometrical center of a capsule type endoscope the point in space in the capsule type endoscope is perceived which corresponds to the center of gravity of an object consisting of solid matter having uniform density and being identical as to its outer shape with the capsule type endoscope.

If a magnetic force is exerted from outside, for instance by an extracorporeal magnet, upon the capsular magnet arranged and oriented in this way, the capsule type endoscope, on the one hand, can be tilted around its cross axis and, on the other hand, can be rotated around its vertical axis. These motions are resulting directly and exclusively from the magnetic interaction between the capsular magnet and the extracorporeal magnet. Furthermore, the arrangement of the capsular magnet according to the invention peripherally both with respect to the actual center of gravity and with respect to the geometrical center of the capsule type endoscope permits the control of the rolling motion of the capsule type endoscope around its longitudinal axis (co-axial axis with respect to the optical axis of the image recording unit). By controlling the orientation of the capsule type endoscope around all three axes of its Cartesian coordinate system in total a three-dimensional movement comparable to an aircraft is possible.

In this context, the following fact is further referred to:

The capsule type endoscope can either freely "float" in a hollow organ or can be adjacent to a hollow organ wall. In the former case the capsule rolls around its longitudinal axis and in the second case the capsule rolls off its point of contact with the organ wall.

Moreover, the capsule type endoscope under real circumstances behaves such that it cannot completely follow a translatory movement of an extracorporeal magnet despite the integrated capsular magnet, as frictional forces between the capsular endoscope and the hollow space wall or obstacles such as plicai or undulations of the hollow space wall can impede a translatory movement of the capsule type endoscope.

In order to apply a magnetic force compensating said rolling motion to the capsule in all events, the intracorporeal (permanent) magnet has to be positioned not only offset with respect to the center of gravity of the capsule but also peripherally with respect to the geometric central axis of the capsule.

The capsule type endoscope preferably includes a cylindrical housing at the one axial end portion of which the image recording unit is arranged so that the longitudinal axis of the housing is substantially aligned with the optical axis of the image recording unit. Such shape promotes the swallowability of the capsule and simultaneously the stability thereof in the intestines of a patient. The image recording unit can be optimally oriented relative to a hollow space area subject to examination.

Furthermore, it has turned out to be of advantage when the energy source is arranged between the image data processing unit and the permanent magnet inside the capsule. It is favorable in this context to build up the energy source of at least one button cell whose respective flat side is oriented in parallel to the longitudinal axis of the housing. In this way, the capsule exhibits an especially small diameter and the center of gravity of the capsule comes close to its geometrical center.

As an alternative, the energy source may also be a device including coils adapted to launch energy by electro-magnetic induction in connection with a corresponding extracorporeal device for generating an oscillating magnetic field. Such systems are known already in prior art and therefore will not be described in detail hereinafter.

In order to move the capsule within a duct-like hollow space an external actuating means is provided including an extracorporeal, preferably permanently acting magnet which is further preferably mounted to a computer-controlled robot arm. A permanent magnet generates a relatively strong magnetic field while having small dimensions and therefore is especially suited for medical use.

Moreover, a magnet of this type may have any shape, for instance cylindrical, conical, elliptical or cubical shape. Preferably such extracorporeal magnet is in the form of a cylinder with the north and south poles being preferably at a radial distance from each other (and not at an axial distance). Consequently, by rotating the extracorporeal magnet around the central axis thereof, the north or south pole of the magnet is rotated more closely toward the patient (to the capsule type endoscope) in response to the angle of rotation and thus exerts a correspondingly higher attractive force upon the respective anti-pole of the capsule type endoscope magnet. In this manner, a tilting motion of the capsule type endoscope, when preferably arranging the capsular magnet in accordance with the invention as afore described, about its cross axis can be effectuated. If such extracorporeal magnet is displaced (in its longitudinal direction) transversely to the capsule type endoscope, the latter follows the movement of the extracorporeal magnet in that the capsule rolls around the longitudinal axis thereof or rolls off the point of contact with the organ wall. Said rolling motion is facilitated by the arrangement of the capsular magnet according to the invention peripherally both with respect to the center of gravity and to the geometrical center of the capsule type endoscope.

The computer is advantageously provided, inter alia, for receiving image data and data about the position of the capsule type endoscope relative to the gravitation and for automatically controlling the robot arm to correct the positional deviation of the capsule type endoscope from a manually settable desired position. This is preferably effectuated by the fact that the inherent computer control performs a correcting movement of the extracorporeal magnet having the afore-described structure, especially a rotation of the extracorporeal magnet around the longitudinal axis thereof for a tilting motion of the capsule type endoscope around the cross axis thereof, and a translatory movement of the extracorporeal magnet in the longitudinal direction thereof (transversely to the capsular magnet) for a rolling motion of the capsule type endoscope around the longitudinal axis of the housing thereof (or roll-off motion). If, accordingly, by a sideward movement of the extracorporeal magnet the capsular endoscope magnet is entrained in a respective direction, the latter would simultaneously perform a tilting motion around the cross axis thereof (about the longitudinal axis thereof) which the computer can automatically correct, however, by rotating the extracorporeal magnet around its longitudinal axis. This is applicable mutatis mutandis to possible rolling motions of the capsule type endoscope around the longitudinal axis thereof which the computer compensates equally independently by displacing the extracorporeal magnet forward and backward (in the longitudinal direction thereof as well as transversely to the polarization of the internal magnet).

In other words, the crucial component parts of the capsule type endoscope are the capsular magnet arranged peripherally (outside the geometrical center and the center of gravity of the capsule) as well as the position sensor, which necessarily results in a specific solution of integrating the other components of the capsule including the particular orientation/arrangement of the energy source in accordance with the foregoing description. Moreover, the means includes the extracorporeal permanent magnet whose position and orientation can be controlled via robotic actors. The computer controls the robotic actors and receives sensor signals (feedback signals) from the position sensor (e.g. tri-axial acceleration sensor) integrated in the endoscopic capsule and from an operator-machine interface through which an operator can enter control instructions for moving the capsule.

Furthermore, the endoscopic device permits a particular control method of the extracorporeal permanent magnet.

The position sensor provided in the endoscopic capsule provides information about the orientation of the capsule relative to the gravitation vector. Said information is processed by the computer and can be converted, in the above-described manner, into correcting movements of the extracorporeal magnet which cannot be directly influenced by the operator in a way that the extracorporeal magnet is moved in the longitudinal and lateral direction while simultaneously rotating around its longitudinal axis, where necessary, until the position sensor reports a desired orientation of the capsule relative to the vertical. These correcting movements facilitate maintaining the relative position between the endoscopic capsule and the extracorporeal permanent magnet within an optimum range for implementing the control instructions entered by the operator.

Hereinafter the invention will be illustrated by way of a preferred embodiment with reference to the accompanying drawings, in which:

FIG. 1a shows a perspective exploded view of a capsule type endoscope in accordance with a preferred embodiment of the invention, FIG. 1b also shows a perspective exploded view of the capsule type endoscope of FIG. 1a from a different perspective, FIG. 2 shows a enlarged view of the internal structure of the capsule type endoscope according to the invention, FIG. 3 shows the entire endoscopic means including the actuating means and the control according to the preferred embodiment of the invention, FIG. 4a, 4b show the capsule type endoscope and an extracorporeal magnet in a construction position relative to each other, FIG. 5a, 5b show the actuating operation for moving the capsule type endoscope along its longitudinal axis, FIG. 5c shows the (compensating) actuating operation for tilting the capsule type endoscope about its longitudinal axis, and FIGS. 6a to 6c show the actuating operation for rolling the capsule type endoscope about its longitudinal axis.

DESCRIPTION OF FIGURES

FIGS. 1a and 1b show the different components of an endoscopic capsule 26 in accordance with a preferred embodiment of the present invention.

Figure 1B:
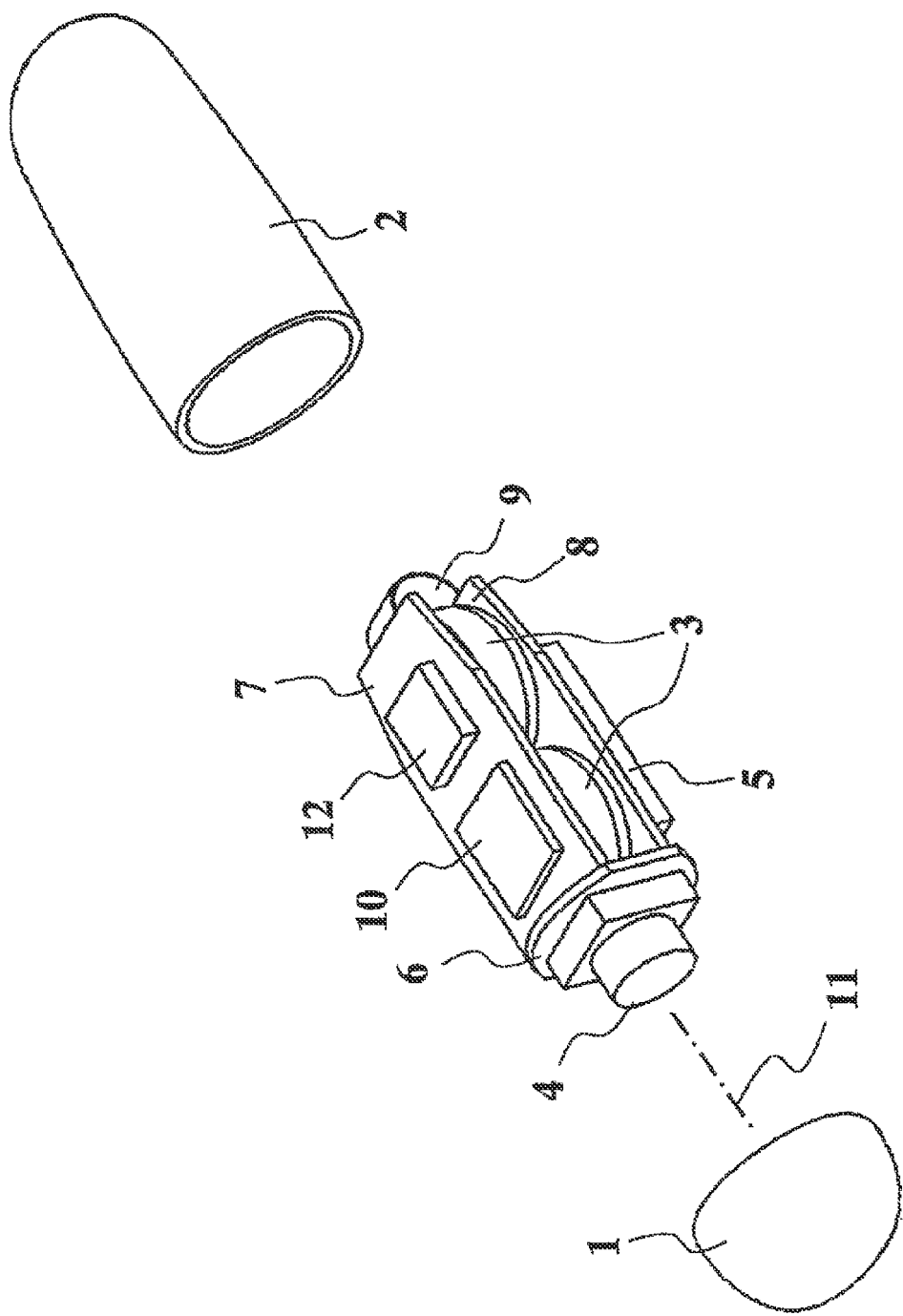

Accordingly, the capsule type endoscope 26 (hereinafter referred to as capsule only) comprises a preferably two-part, substantially cylindrical housing having a receiving housing member 2 to the one end side of which a cap member 1 made of translucent material is attached. In the receiving member 2 of the capsule housing the electronic component parts and the energy source of the capsule 26 are accommodated. They comprise an image recording unit, an optical system 4 in the present case, which is applied to a photosensitive sensor (CMOS chip) soldered in turn to an electric printed circuit board 6. The printed circuit board 6 for the image generating unit is oriented so that the optical axis of the optical system 4 is oriented coaxially with respect to the central axis of the capsule housing and faces the translucent cap 1. The printed board 6 is preferably arranged normal to the central axis of the capsule.

Immediately behind the printed board 6 of the image generating unit, two further printed boards 7, 8 maintained at a distance in parallel to each other are disposed at right angles with respect to the printed board 6. The one printed board 7 according to FIG. 1b supports a data processing unit 10 and a data transmission unit 12. The other printed board 8 according to FIG. 1a is equipped with a position sensor 16 to determine the position of the capsule with respect to a gravitation vector. Furthermore, a permanent magnet 5 oriented such that its north-south axis extends coaxially with respect to the central axis 11 (equally the optical axis) of the capsule housing is positioned on the printed board 8 in an electrically insulated manner. An energy source in the form of two button cell batteries 3 is arranged between the two printed boards 7 and 8 such that the respective flat sides thereof are oriented in parallel to the printed boards 7, 8. The two button cells 3 are spaced apart in the longitudinal direction of the capsule housing. Finally a connection of the printed boards is provided in the form of a data bus 9 interconnecting the two electric printed boards 7, 8 for exchange of information.

Figure 2:
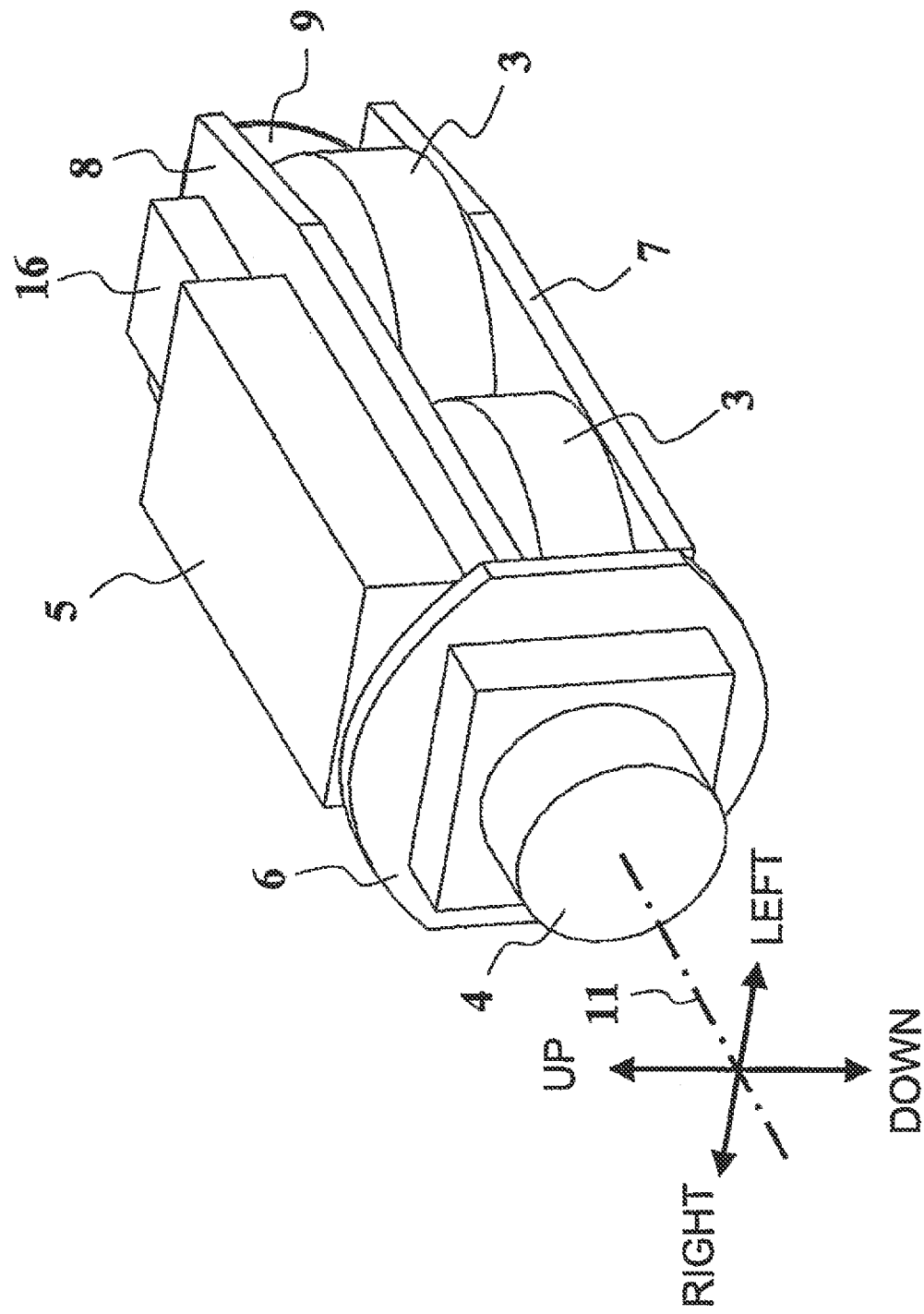

As it is more clearly shown in FIG. 2, the optical axis of the image generating unit (camera) 4 is arranged in parallel to the X-axis (central axis) 11 of the capsule 26 to be preferably aligned with the same. Consequently, the camera image shows upper, lower, left and right edges (see FIG. 2). The upper edge of the camera image corresponds to an upper edge of an endoscopic image displayed on a screen 18 according to FIG. 3.

As already described in the foregoing, the permanent magnet 5 is disposed in parallel to the optical axis 11 of the capsule at an upper edge of the capsule 26. The upper edge of the capsule 26 preferably refers to the side of the capsule 26 corresponding to the upper edge of the endoscopic image. This peripheral arrangement of the permanent magnet 5 causes the permanent magnet 5 to be spaced apart from the geometrical center or the central axis of the capsule housing as well as from the center of gravity of the entire capsule 26. The longitudinal arrangement of the permanent magnet 5 is therefore facilitated by the afore-mentioned orientation of the other components, especially the two printed boards 7 and 8 and the button cells 3 arranged in series in the longitudinal direction of the capsule 26.

Other than in previously known endoscopic capsules, the batteries 3 are juxtaposed or arranged in series in the central X-Y plane of the capsule 26. In this way, the center of gravity of the endoscopic capsule 26 is shifted to the vicinity of the central axis.

Figure 3:
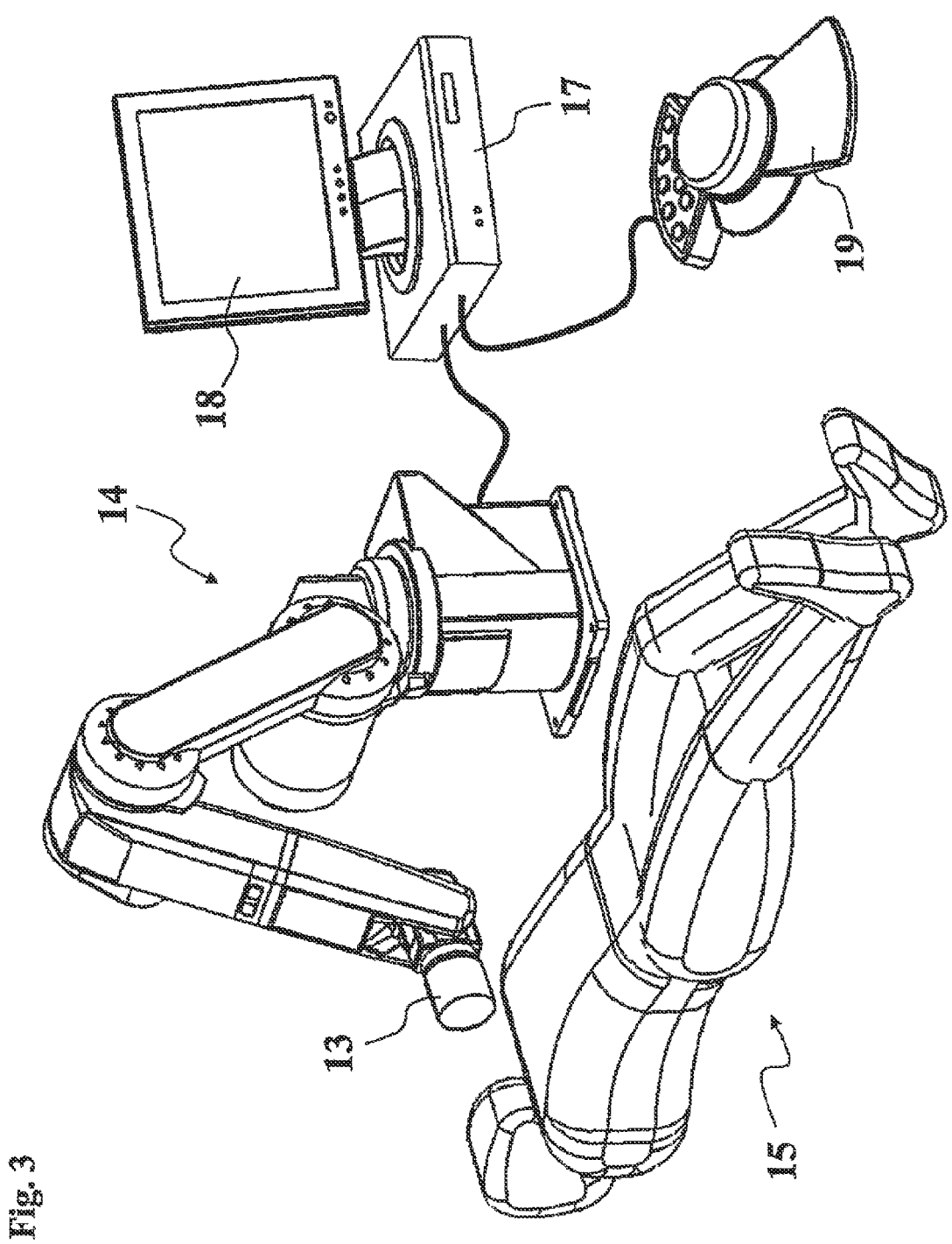

FIG. 3 shows the entire endoscopic means and the entire endoscopic system comprising the endoscopic capsule 26 described in more detail in the foregoing which has already been introduced into the gastro-intestinal tract of a schematically represented patient 15, a robot arm 14 controlling an extracorporeal permanent magnet 13 which is pivotally and rotatably mounted to the distal end of the robot arm 14, a computer 17 having a connected endoscopic screen 18 as well as an operator-machine-interface 19 in the form of a handheld or a keyboard.

As one can further take from FIG. 3, the keyboard 19 is connected to the computer 17 for data exchange either via cable or via remote control. The computer 17 in turn is connected to the robot arm 14 via an electric cable. In addition, a receiving means not shown in detail is connected to the computer 17 for receiving image and position data as they are emitted by the data transmission unit 12 within the capsule 26.

Figure 4A:
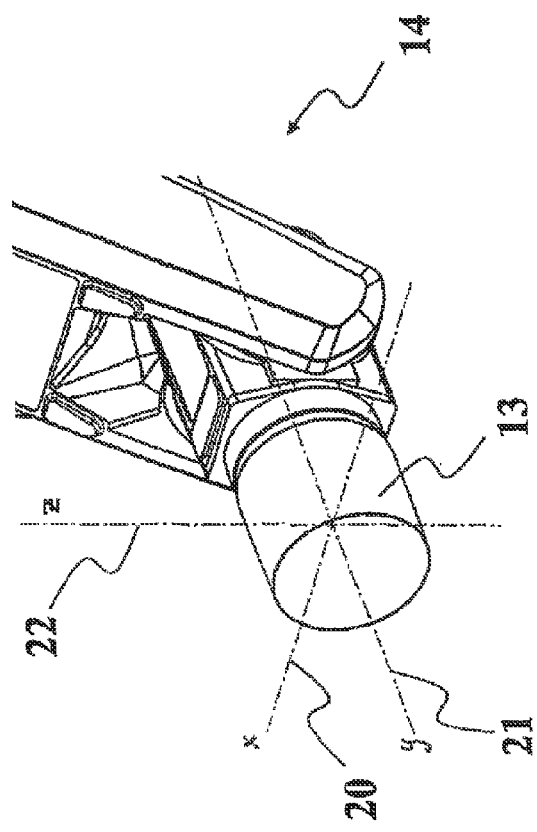
Figure 4B:
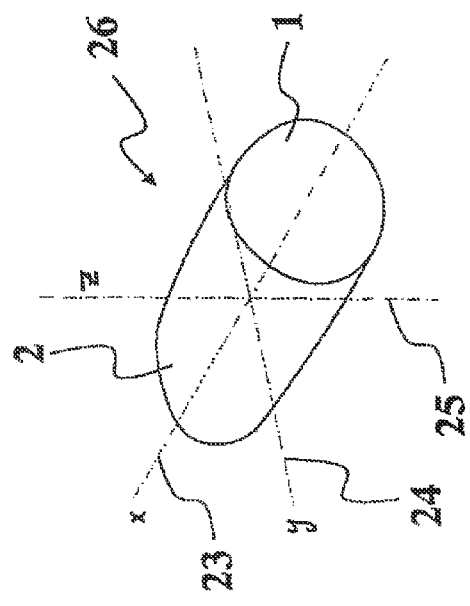

The FIGS. 4a and 4b show an enlarged view of the capsule 26 schematically represented there as well as the extracorporeal permanent magnet 13 in a predetermined (desired) position relative to each other. Accordingly, the extracorporeal permanent magnet 13 has a cylindrical shape with a Y-axis 21 extending in the longitudinal direction of the permanent magnet 13, an X-axis 20 at right angles hereto and a vertically extending Z-axis 22. Equally, at the capsule 26 comprising the translucent cover cap 1 and the receiving member 2 a coordinate system consisting of an X-axis 23 extending along the capsule 26, a transversely extending (horizontal) Y-axis 24 and a vertically extending Z-axis 25 is drawn. Moreover, the relative position between the cylindrical extracorporeal permanent magnet 13 and the capsule housing in accordance with FIGS. 4a and 4b is not random but is shown at a predetermined (desired) position. Accordingly, the Y-axis 21 (central axis) of the extracorporeal permanent magnet 13 is arranged coaxially with respect to the Y-axis 24 (which is normal to the central axis) of the capsule. Consequently, the extracorporeal permanent magnet 13 extends at right angles with respect to the capsule housing 1, 2 of the capsular endoscope 26.

In the embodiment described here the Y-axis 21 of the extracorporeal magnet 13 is generally supposed to be horizontal.

In the relative position shown according to FIGS. 4a and 4b the endoscopic capsule is at a magnetic equilibrium of forces. That is to say that the capsule 26 adopts an exactly right-angled orientation with respect to the extracorporeal permanent magnet 13 and is simultaneously aligned horizontally both in the X-axis and in the Y-axis.

Accordingly, from FIG. 4a and FIG. 4b a particular control method is resulting for controlling the endoscopic capsule 26 as illustrated especially in detail in the FIGS. 5a to 6c.

Consequently, the polarization (north-south axis) of the extracorporeal permanent magnet 13 is selected such that it extends in parallel to the X-axis 20 (cross axis) of the extracorporeal permanent magnet 13. As explained in the foregoing already, the polarization of the (intracorporeal) permanent magnet 5 inside the capsule is selected such that it extends in parallel to the X-axis 23 (longitudinal axis) of the capsule 26. Herefrom results the afore-described orientation of the capsule 26 relative to the extracorporeal cylindrical permanent magnet 13 as shown in FIGS. 4a and 4b.

The control method especially in accordance with the FIGS. 5a and 5b serves for compensating the tilting motion of the capsule 26 around the Y-axis 24 thereof as an artifact motion upon a control instruction entered by an operator via the operator-machine interface 19 for a translatory movement of the capsule 26 in the longitudinal direction of the capsule. Said artifact motion is represented in FIG. 5b.

Concretely speaking, FIG. 5a shows the orientation of the capsule 26 and its X-axis 23 (longitudinal axis) in the event that the extracorporeal permanent magnet 13 is provided directly above the same and the polarization of the extracorporeal magnet 13 is horizontal. Accordingly, the capsule 26 orients itself so that the polarization of the permanent magnet 5 within the capsule is anti-parallel to that of the extracorporeal permanent magnet 13.

FIG. 5b shows the effect on the orientation of the capsule 26 when the extracorporeal permanent magnet 13 moves relative to the capsule 26 along its X-axis 20, viz. in the longitudinal direction of the capsule 26, starting out from the (desired) situation as shown in FIG. 5a. In this case the capsule 26 tilts or inclines around its cross axis, viz. around its Y-axis 24, so that an angle forms between the X-axis 23 of the capsule 26 and the horizontal. This change of position is registered by the position sensor 16 inside the capsule. These sensor data are simultaneously made available also to the computer 17.

FIG. 5c now illustrates a first correcting movement of the extracorporeal permanent magnet 13 corresponding to the control method according to the invention which is automatically performed by the computer 17 without any influence by the operator.

Accordingly, the computer 17 controls the robotic actors (not shown) on the basis of the sensor signals of the position sensor 16 inside the capsule taking the control signals of the operator into consideration which have been entered into the computer 17 via the operator-machine-interface 19. In accordance with this control of the robotic actors, the extracorporeal permanent magnet 13 is rotated (rolled) in the present case around its Y-axis 21 (corresponding to its longitudinal axis) such that the endoscopic capsule 26 is tilted around its Y-axis 24, i.e. about the longitudinal axis 23 thereof, until the tilting motion of the endoscopic capsule 26 caused by the translatory movement of the extracorporeal permanent magnet 13 along its X-axis 20 (cf. FIG. 5b) is compensated. This state is shown in FIG. 5c.

On principle, this control method works equally for each home position of the capsule 26 with respect to its tilting position of the X-axis 23 relative to the horizontal. The position of the capsule 26 relative to the extracorporeal magnet 13 shown in FIGS. 4a and 4b as home position therefore is only one possible home position. Especially by rotation of the extracorporeal magnet 13 around its Y-axis 21 a different home position which is frequently encountered is resulting in which the capsule 26 is rotated ant-parallel around its Y-axis 24.

In an advantageous further development of said control method the computer 17 additionally controls the robotic actors such that with an appropriate input of control signals by the operator for a translatory movement of the capsule 26 in the longitudinal direction of the capsule for the purpose of minimizing the artifact movement of the capsule 26 (rotation around the Y-axis 24 of the capsule 26) the extracorporeal permanent magnet 13 performs a (coupled) tilting motion around its Y-axis 21 in addition to the translatory movement along its X-axis 20. Said (basic) tilting motion is not based on sensor signals of the position sensor 16 provided inside the capsule but serves for approximately minimizing the artifact movement of the capsule 26 in advance and thus constitutes a kind of feed forward control. The further compensation of the artifact movement of the capsule 26 is performed, as aforedescribed, on the basis of the sensor data of the position sensor 16 provided inside the capsule.

In another advantageous development of this control method the computer 17 calculates, on the basis of the difference between the angle formed between the X-axis 20 of the extracorporeal magnet 13 and the horizontal and the angle formed between the X-axis 23 of the capsular endoscope and the horizontal, an approximate relative deviation of the position of the extracorporeal magnet 13 from the position vertically above the capsule 26. The angle of the X-axis 23 of the capsule 26 is known to the computer 17 from the sensor data of the position sensor 16 inside the capsule. The angle of the X-axis 20 of the extracorporeal magnet 13 is known to the computer on the basis of the feed back from the sensor and position data from the robotic actors. In case that the extracorporeal magnet 13 is disposed vertically above the capsule 26, the angle formed between the X-axis 20 of the extracorporeal magnet 13 and the horizontal is equal according to amount to the angle formed between the X-axis 23 of the capsule 26 and the horizontal. Unless the extracorporeal magnet 13 is positioned vertically above the capsule 26, a deviation according to amount results between the angle formed between the X-axis 20 of the extracorporeal magnet 13 and the horizontal and the angle formed between the X-axis 23 of the capsular endoscope and the horizontal which allows to conclude the direction and the approximate deviation of the extracorporeal magnet 13 from the position vertically above the capsule 26. On the one hand, this information can be made available to the operator e.g. via a graphical or numerical display on the endoscopic monitor. On the other hand, this information can be used for the purpose that in the case of appropriate control signals the computer 17 controls the robotic actors through the operator such that the extracorporeal magnet 13 is oriented vertically above the capsule 26.

FIG. 6 shows another control method for controlling the endoscopic capsule 26 according to the invention.

The polarization of the extracorporeal permanent magnet 13 is selected, as already explained in the foregoing, so that it extends in parallel to the X-axis 20 of the extracorporeal permanent magnet 13. The polarization of the capsular magnet 5 is further selected such that it extends in parallel to the X-axis 23 of the capsule 26. The control method according to FIG. 6 serves for automatically orienting the extracorporeal permanent magnet 13 along its Y-axis 21 by computer control vertically above the endoscopic capsule 26 such that the Y-axis 24 of the capsule 26 is provided in the horizontal.

FIG. 6a shows the orientation of the capsule 26 as well as its Y-axis 24 in case that the extracorporeal permanent magnet 13 is provided vertically above the same and the polarization of the extracorporeal permanent magnet 13 is horizontal. The capsule 26 orients itself such that the polarization of the permanent magnet 5 provided inside the capsule is anti-parallel to that of the extracorporeal permanent magnet 13, i.e. the Y-axis 24 of the capsule 26 is oriented horizontally.

FIG. 6b shows the effect on the orientation of the capsule 26 when the extracorporeal permanent magnet 13 moves along its Y-axis 21 relative to the capsule 26 (i.e. in the sideward direction of the capsule 26), starting out from the situation as shown in FIG. 6a. In this case the capsule 26 rolls around its X-axis 23 (central axis of the capsule housing) so that an angle forms between the Y-axis 24 of the capsule 26 and the horizontal. This change of position is equally registered by the position sensor 16 provided inside the capsule and appropriate sensor data are made available to the computer 17.

Consequently FIG. 6c shows a correcting movement of the extracorporeal permanent magnet 13 corresponding to the control method according to the invention. The computer 17 thus controls the robotic actors based on the sensor signals from the position sensor 16 automatically as well as taking the control signals entered by the operator into account. In accordance with this control of the robotic actors, therefore the extracorporeal magnet 13 is moved along its Y-axis 21 such that the endoscopic capsule 26 rotates around its X-axis 23 (rolling motion) until the rotation (rolling motion) of the endoscopic capsule caused by the movement of the extracorporeal magnet 13 along its Y-axis 21 (cf. FIG. 6b) is compensated.

As can be seen from the foregoing description, there is the possibility of compensating an induced tilting motion as well as rolling motion of the capsule by an automatic computer-controlled movement of the extracorporeal magnet 13 due to the special arrangement of the capsule magnet 5 inside the capsule 26 according to the invention. The position sensor 16 provided inside the capsule serves for concluding the position of the capsule 26 relative to the extracorporeal magnet 13 from the information of position inferred therefrom. In this way the orientation of the capsule 26 about all three axes of its Cartesian coordinate system can be controlled. This permits a guiding of the capsule type endoscope 26 stable in all axes of space via the control of a magnetic field generated by an extracorporeal magnet (preferably permanent magnet) 13. Moreover, the extracorporeal magnet 13 can be automatically positioned vertically above the capsule 26 based on the sensor data of the position sensor 16 provided inside the capsule so that even localizing the capsule 26 in the horizontal plane is facilitated.

The invention claimed is:

1. A method, comprising:
utilizing an actuator to correct positioning of an endoscope, the actuator having a moveable extracorporeal magnet mounted to an arm, the extracorporeal magnet having a north-south polarization axis, the endoscope including:
an image recording unit and an image data processing unit,
a position sensor for providing data about the positioning of the endoscope relative to a gravitation vector,
a data transmitting unit, and
an energy source for supplying energy to the image recording unit, the image data processing unit, the data transmitting unit, and the position sensor, and
an internal magnet, the internal magnet having a north-south polarization axis forming one resulting magnetic field, wherein the internal magnet with its one resulting magnetic field are positionally offset relative to the center of gravity of the endoscope, and the north-south polarization axis of the internal magnet and its one resulting magnetic field are positionally offset relative to the longitudinal central axis of the endoscope,
orienting the extra corporeal magnet with respect to the internal magnet such that the respective longitudinal central axes of the extracorporeal magnet and the internal magnet are always substantially perpendicular, while the respective north-south polarization axes of the extra corporeal magnet and the internal magnet are substantially aligned and anti-parallel,
detecting a gravitational orientation of the endoscope relative to the gravitation vector by utilizing the position sensor,
changing a location of the endoscope by moving the extracorporeal magnet along one or more of a direction substantially along the north-south axis of the extra corporeal magnet, or a direction substantially transverse thereto,
compensating for tilt induced in the endoscope around an axis transverse to its longitudinal central axis and with respect to its detected gravitational orientation, due to the changing of the location of the endoscope by the movement of the extra corporeal magnet, by tilting the extra corporeal magnet around an axis transverse to its north-south polarization axis, and
compensating for rolling of the endoscope around its longitudinal central axis and with respect to its detected gravitational orientation, due to the changing of the location of the endoscope by the movement of the extra corporeal magnet, by displacing the extra corporeal magnet transversely with respect to the longitudinal central axis of the endoscope.

2. The method of claim 1, wherein a displacement of the extracorporeal magnet at least partially horizontally and along the longitudinal central axis of the endoscope is coupled with a tilting motion of the extracorporeal magnet about its north-south polarization axis such that an influence of the relative position between the extracorporeal magnet and the endoscope on the tilted position of the capsule type endoscope about the longitudinal central axis thereof is minimized.

3. The method of claim 1, wherein a relative position between the extracorporeal magnet and the endoscope can optionally be adjusted.

* * * * *